(12) United States Patent
Moen et al.

(10) Patent No.: US 10,993,629 B2
(45) Date of Patent: May 4, 2021

(54) MULTI-FOCAL INTRAVASCULAR PRESSURE CATHETER DEVICES, SYSTEMS AND METHODS

(71) Applicant: Regents of the University of Minnesota, Minneapolis, MN (US)

(72) Inventors: Sean Lester Moen, St. Paul, MN (US); Andrew Misselt, Edina, MN (US); Jack Stubbs, Orlando, FL (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 537 days.

(21) Appl. No.: 15/136,319

(22) Filed: Apr. 22, 2016

(65) Prior Publication Data

US 2016/0310026 A1    Oct. 27, 2016

Related U.S. Application Data

(60) Provisional application No. 62/151,696, filed on Apr. 23, 2015.

(51) Int. Cl.
*A61B 5/0215* (2006.01)
*A61B 5/00* (2006.01)

(52) U.S. Cl.
CPC ........ *A61B 5/02158* (2013.01); *A61B 5/6852* (2013.01); *A61B 2562/0247* (2013.01); *A61B 2562/12* (2013.01)

(58) Field of Classification Search
CPC ..... A61B 5/0215; A61B 5/00; A61B 5/02158; A61B 5/6852; A61B 2562/12; A61B 2562/0247

See application file for complete search history.

(56) References Cited

U.S. PATENT DOCUMENTS

| | | | |
|---|---|---|---|
| 7,472,601 B1* | 1/2009 | Tenerz | A61B 5/0215 600/585 |
| 9,149,230 B2* | 10/2015 | Caron | G01F 1/6884 |
| 2006/0271029 A1* | 11/2006 | Abboud | A61B 18/02 606/21 |
| 2007/0282211 A1* | 12/2007 | Ofek | A61B 5/0215 600/523 |

(Continued)

*Primary Examiner* — Eric J Messersmith
(74) *Attorney, Agent, or Firm* — Patterson Thuente Pedersen, P.A.

(57) ABSTRACT

Embodiments relate to multi-focal intravascular pressure catheters and related systems and methods. In an embodiment, a catheter comprises a plurality of pressure sensors spaced apart along at least a portion of the catheter. Each of the plurality of pressure sensors can comprise a pressure membrane arranged over an aperture in the catheter. In an embodiment, the pressure membrane can comprise carbon nanotubes, silver or gold nanoparticles, or another suitable material that can provide a signal in response to a mechanical change (e.g., deformation or flexing of the pressure membrane) to indicate a pressure or change in pressure. Signals from the plurality of pressure sensors can be communicated to an electrical interface which can calibrate or convert the signals into a visual indication of the pressure at any one of the plurality of pressure sensors as well as pressure gradients between various ones of the plurality of pressure sensors.

18 Claims, 6 Drawing Sheets

(56) References Cited

U.S. PATENT DOCUMENTS

| | | | |
|---|---|---|---|
| 2013/0228018 A1* | 9/2013 | Mouchel La Fosse | ....................... A61B 5/02158 73/753 |
| 2014/0180030 A1* | 6/2014 | Dorando | .............. A61B 5/0215 600/301 |
| 2015/0351645 A1* | 12/2015 | Hiltner | ............... A61B 5/02156 600/486 |
| 2017/0319326 A1 | 11/2017 | Rosenberg | |

\* cited by examiner

MULTI-FOCAL INTRAVASCULAR PRESSURE CATHETER DEVICES, SYSTEMS AND METHODS

RELATED APPLICATION

The present application claims the benefit of U.S. Provisional Application No. 62/151,696 filed Apr. 23, 2015, which is incorporated herein by reference in its entirety.

TECHNICAL FIELD

Embodiments relate generally to catheters and more particularly to catheters and related systems and methods to measure intravascular pressure and pressure changes.

BACKGROUND

Intravascular pressure is the pressure of the blood within an artery or vein of the body and can refer to intraarterial pressure (i.e. pressure of the blood within an artery of the body) or intravenous pressure (i.e. pressure of the blood within a vein of the body). Intravascular pressure can be affected by many factors, including arterial stenosis, which is a narrowing of an artery. Narrowing of an artery restricts blood flow through the artery, leading to higher pressure. Stenosis can be treated or relieved in several ways, including by the placement of stents, clearing of blockages, administration of drugs and other treatments and therapies. These treatments and therapies can vary depending on the location of the stenosis. For example, some treatments are specific to the heart, such as for treatment of aortic valve stenosis. Others relate to treatment of peripheral vascular disease (PVD), which refers to blood vessel disease outside of the heart and brain and can include peripheral artery disease (PAD), which occurs when the arteries that supply blood to the internal organs, arms or legs become partially or completely blocked. Particular examples of PVD or PAD include iliac to popleteil artery stenosis, hepatic arterial stenosis and femoral artery stenosis, among many others.

Intravascular pressure measurements and gradients (i.e., changes in pressure measurements between different locations within an artery or vein) are universal metrics currently used to quantify the severity of a stenotic region prior to and after intervention. These measurements can be particularly important in the diagnosis and treatment of PVD. Conventional pressure measurement devices typically are guidewires with pressure sensitive tips that can measure the pressure at a single point in a vessel (i.e., at the location of the pressure sensitive tip), or end hole catheters that measure pressure via a pressure transducer at the end hole thereof.

In an example of a current process using such a conventional end hole catheter pressure measurement device, a physician directs a 5 French angiographic catheter proximal to the diseased area of vasculature, such as a femoral artery stenosis. The physician then injects iodinated contrast to assess the severity of the disease. Next, the catheter is advanced to a non-diseased section of the artery distal to the stenotic region of interest. This location and a pressure measurement there will serve as a gauge to assess the successfulness of the procedure. A pressure transducer is placed at the same level as the patient's cardiac notch and connected to the patient monitoring system. A nurse then selects a hemodynamic display setting on the monitor and "zeroes" the transducer by flushing the system with normal saline. Then the 5 French angiographic catheter is connected to the pressure transducer and the first measurement is made and documented. The physician pulls back the catheter, stopping at segments momentarily in order to document pressure. When all of the necessary pressure measurements are made and documented, a pressure gradient can be calculated from the individual measurements.

The conventional devices used in this process and others like it, as well as the process itself, suffer from several inadequacies, particularly when used in the peripheral vasculature. These inadequacies include a fragile guidewire (e.g., a 0.014 guidewire, which may be suited to delicate cardiac work but cannot hold up in more robust peripheral uses), low maximum vessel diameter for accurate pressure measurement (e.g., 5 mm, which is generally too small for peripheral uses), the aforementioned single focal pressure measurement at any time, and lack of a stable working platform for device delivery or intervention that does not require wire exchange.

SUMMARY

Embodiments relate to multi-focal intravascular pressure catheters and related systems and methods. In an embodiment, a catheter comprises a plurality of pressure sensors spaced apart along at least a portion of the catheter. Each of the plurality of pressure sensors can comprise a pressure membrane arranged over an aperture in the catheter. In an embodiment, the pressure membrane can comprise carbon nanotubes, silver nanoparticles, gold nanoparticles or another suitable material that can provide a signal in response to a mechanical change (e.g., deformation or flexing of the pressure membrane) to indicate a pressure or change in pressure. Signals from the plurality of pressure sensors can be communicated to an electrical interface which can calibrate or convert the signals into a numeric indication of the pressure at any one of the plurality of pressure sensors as well as pressure gradients between various ones of the plurality of pressure sensors. The numeric indication can be displayed or otherwise provided, such as by a graphical user interface (GUI) of a computer device communicatively coupled with the electrical interface.

The above summary is not intended to describe each illustrated embodiment or every implementation of the present invention. The figures and the detailed description that follow more particularly exemplify these embodiments.

BRIEF DESCRIPTION OF THE DRAWINGS

Embodiments may be more completely understood in consideration of the following detailed description in connection with the accompanying drawings, in which.

While embodiments are amenable to various modifications and alternative forms, specifics thereof have been shown by way of example in the drawings and will be described in detail. It should be understood, however, that the intention is not to limit to be limited to or by the particular embodiments depicted and described. On the contrary, the intention is to cover all modifications, equivalents, and alternatives falling within the spirit and scope of the appended claims.

DETAILED DESCRIPTION

Embodiments relate to multi-focal intravascular pressure catheters and related systems and methods for sensing or measuring pressure at a plurality of locations in an artery, vein or other location.

As used herein unless otherwise noted, "distal" generally refers to the delivery or insertion end or portion of the catheter, remote from the physician or medical professional controlling the catheter, while "proximal" generally refers to the opposite end, the one closer to the physician or medical professional.

Figure 1:
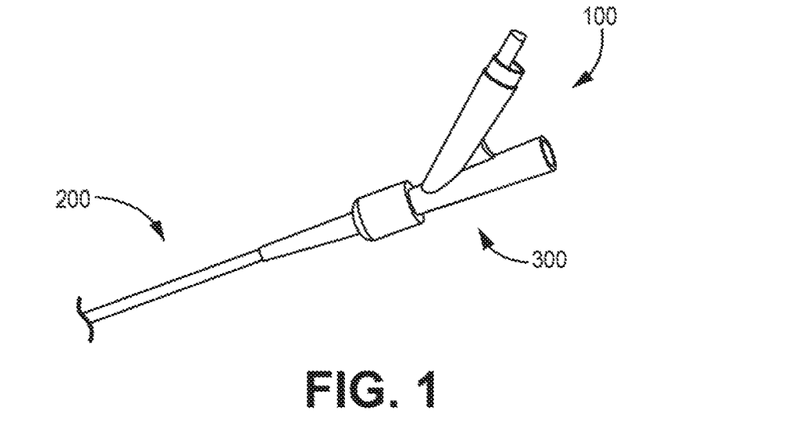
FIG. 1 is a perspective view of a proximal hub of a catheter according to an embodiment.

Referring to FIG. 1, a catheter 100 is depicted. Catheter 100 is a multi-focal pressure catheter, comprising a plurality of pressure sensors along its length such that intravascular pressures can be sensed simultaneously at each pressure sensor location along catheter 100.

Catheter 100 is a device that can be routed through a vein, artery, or other area to a desired site of treatment or measurement. The size of catheter 100 can vary; for example, in one embodiment catheter 100 can comprise a 5 French catheter, though larger or smaller diameters can be implemented in other embodiments. For example, a 3 French catheter could be used in some neurovascular applications. The overall length of catheter 100 also can vary, such as being at least about 40 cm in embodiments, for example at least about 60 cm in some embodiments, such as 90 cm or more in other embodiments. In general, the size of the catheter can relate to the application and/or area of the body for treatment, and embodiments of catheter 100 can be suitable for many different applications and/or areas, such that the size can vary accordingly. In an embodiment, catheter 100 comprises a distal portion 200 and a proximal portion 300.

Figure 2:
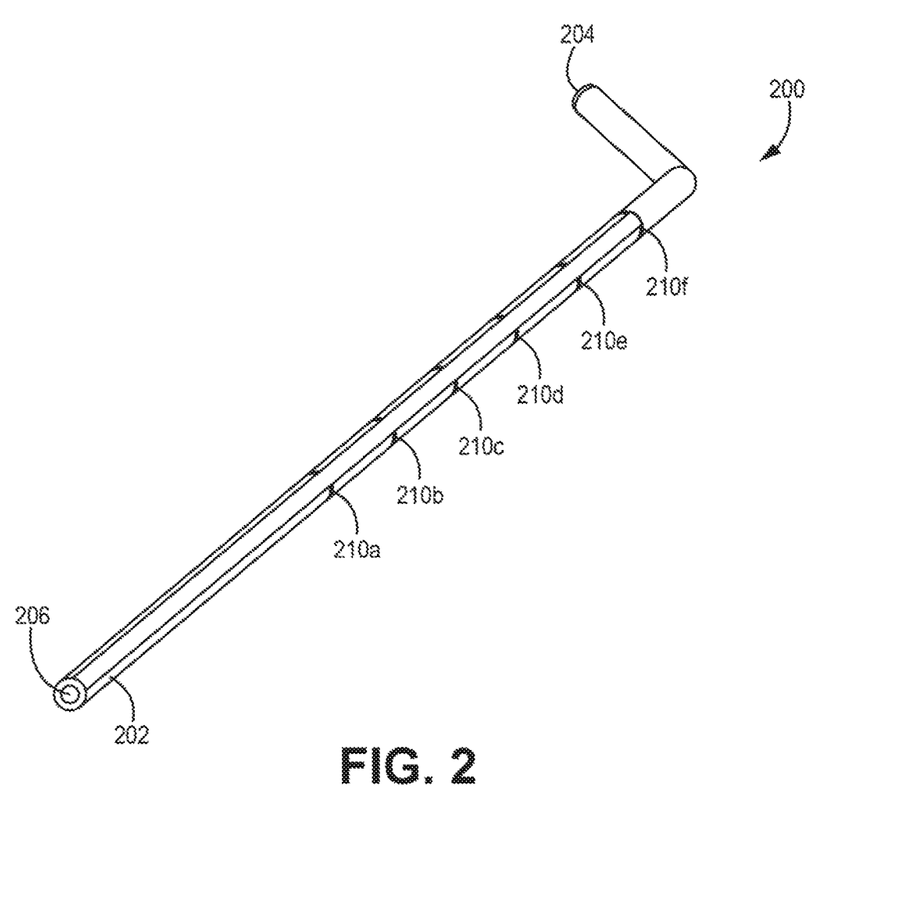
FIG. 2 is a perspective view of a distal portion of a catheter according to an embodiment.

Referring to FIG. 2, an embodiment of distal portion 200 of catheter 100 is depicted. Distal portion 200 comprises a proximal end 202 and a distal end 204. Proximal end 202 is configured to interconnect with proximal portion 300 of catheter 100. Distal end 204 is configured to be inserted into a vein, artery or other area and thus is generally flexible in order to allow insertion and manipulation but also sufficiently rigid in order to enable a clinician to advance catheter 100 to a treatment site. Distal portion 200 comprises a central lumen 206 through which fluids, gases, surgical instruments and other substances and devices can be conveyed to the treatment site at distal end 204 or another location along distal portion 200. In other embodiments, distal portion 200 can have dual lumens, such as concentric outer and inner lumens, with the pressure sensors discussed infra arranged in the outer lumen and the inner lumen used for fluid, gas or instrument conveyance.

In embodiments, distal portion 200 further comprises a plurality of pressure sensors 210a-210f. Pressure sensors 210a-210f are spaced apart from one another along distal portion 200 of catheter 100. In some embodiments, pressure sensors 210a-210f are regularly spaced apart from one another, such as by about 1 millimeter (mm) to about 10 centimeters (cm). In other embodiments, pressure sensors 210a-210f can be irregularly spaced, such as further apart from one another near proximal end 202 and closer together near distal end 204. FIG. 2 depicts six pressure sensors 210a, 210b, 210c, 210d, 210e and 210f, but in other embodiments more or fewer pressure sensors 210n can be implements. For example, in one embodiment distal portion 200 comprises two pressure sensors 210a and 210b (though their positions between proximal end 202 and distal end 204, and their relative positions, can vary from those depicted in FIG. 2), while in other embodiments distal portion 200 can comprise thirty or more pressure sensors 210n. The number of pressure sensors can be selected according to a type of treatment, a compatibility of pressure sensors 210n with a user interface or software tool configured to be coupled to catheter 100 to provide output data, technological factors related to materials and components of catheter 100, and/or some other factor(s). The embodiment depicted and discussed herein comprising six pressure sensors 210a-210f is only one example, without limitation with respect to other embodiments.

Figure 3:
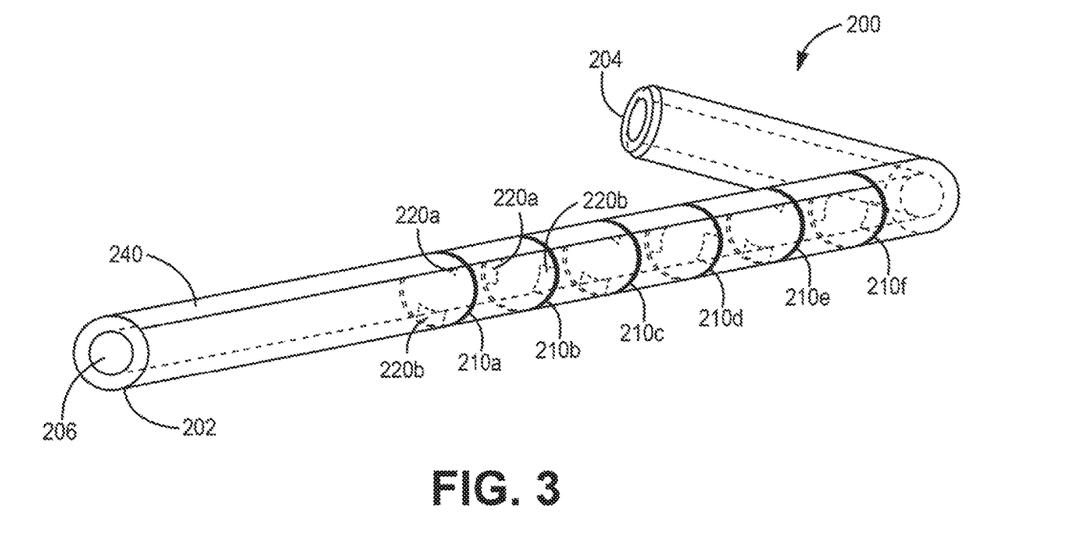
FIG. 3 is a partially transparent perspective view of a distal portion of a catheter according to an embodiment.

Referring to FIG. 3, each pressure sensor 210a-210f comprises at least one aperture extending through the wall of distal portion 200 to lumen 206. In the embodiment of FIG. 3, each pressure sensor 210a-210f comprises two apertures 220a and 220b arranged opposite each other on the circumference of distal portion 200 (e.g., with the center of each aperture 220a and 220b spaced apart by 180 degrees along the circumference of distal portion 200). Apertures 220a and 220b can be of varying sizes, such as having a diameter of about 0.01 inches to about 0.025 inches in embodiments, though apertures 220a and 220b need not be round (e.g., need not have a diameter or circumference, in which case the size can be measured with respect to a lateral dimension of the aperture) in every embodiment. Apertures 220a and 220b also can be larger or smaller in other embodiments, such as for other applications. Apertures 220a and 220b generally extend all the way through the wall of distal portion 200 and thus are about 0.01 inches to about 0.03 inches deep in the depicted embodiment, though in some embodiments apertures 220a and 220b are deeper according to the thickness of the catheter.

The apertures of adjacent pressure sensors, e.g., 210a and 210b, are rotated 90 degrees with respect to one another. In other words, if apertures 220a and 220b of pressure sensor 210a are centered at 0 degrees and 180 degrees, respectively, then apertures 220a and 220b of pressure sensor 210b are centered therebetween at 90 degrees and 270 degrees, respectively. Pressure sensor 210c has the same aperture configuration as pressure sensor 210a in this embodiment, pressure sensor 210d has the same aperture configuration as pressure sensor 210b, and so on to the last pressure sensor 210n.

The number, size and arrangement of apertures 220a and 220b can vary in other embodiments. For example, in another embodiment apertures 220a and 220b of each pressure sensor 210n can be arranged at the same general positions along the circumference of distal portion 200, or one or more of the pressure sensors 210n can comprise more or fewer apertures, or some other configuration or arrangement can be implemented. Though a minimum of one aperture 220 can be used at any pressure sensor 210*n*, having at least two apertures 220*a* and 220*b* can be advantageous in case one aperture 220*a* or 220*b* should be positioned against an artery wall or otherwise become blocked by tissue and unable to provide any or an accurate measurement. Having more than two apertures also can be desirable in some applications, though such a configuration also can increase the complexity of components and circuitry of catheter 100 and its related system for communicating data and measurements.

Figure 4A:
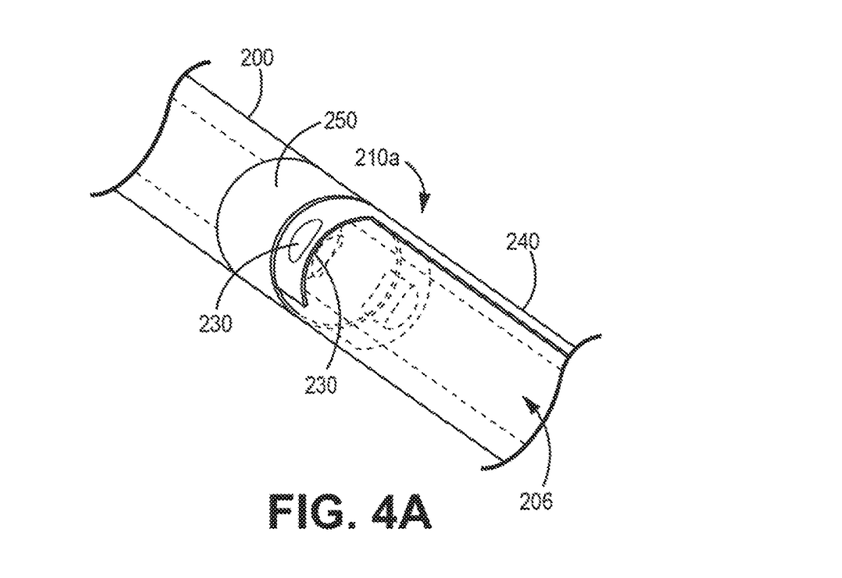
FIG. 4A is a partially transparent detail perspective view of a segment of a distal portion of a catheter according to an embodiment.
Figure 4B:
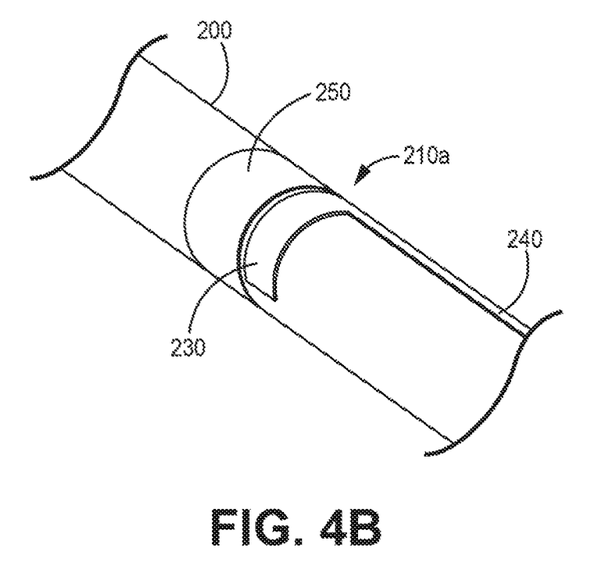
FIG. 4B is a perspective detail view of the segment of FIG. 4A.
Figure 5:
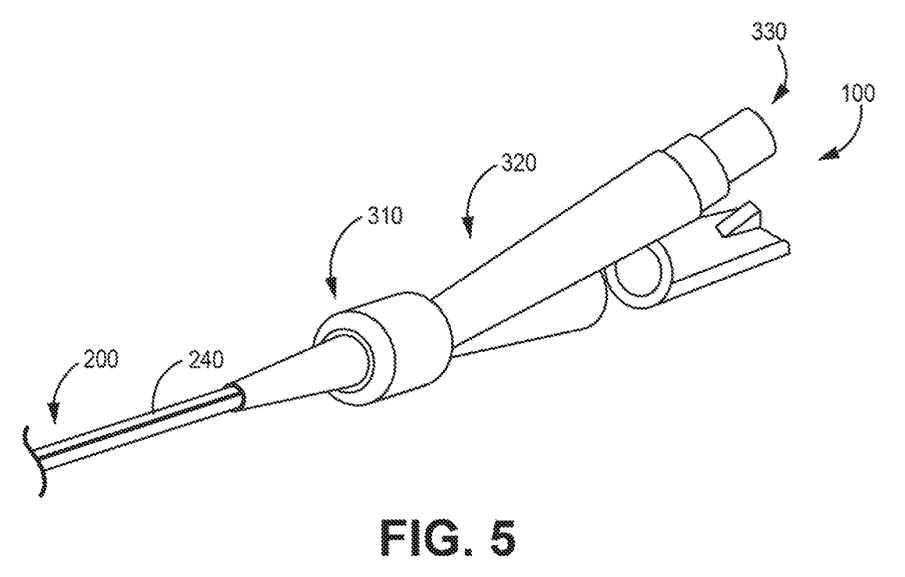
FIG. 5 is a perspective view of part of the proximal hub of a catheter according to an embodiment.

Referring also to FIGS. 4A and 4B, each aperture 220*a*, 220*b* of each pressure sensor 210*a*-210*f* is covered by a pressure membrane 230 coupled to a signal strip 240. Signal strip 240 is electrically coupled with each pressure sensor 210*a*-210*f*. Adjacent or proximate each pressure sensor 210*a*-210*f* is a radiopaque band 250. In use, radiopaque band 250 enables a physician or clinician using catheter 100 to visually confirm the location of distal portion 200 and/or a particular pressure sensor 210*a*-210*f* using a fluoroscope. This can be helpful in confirming that a pressure sensor 210*a*-210*f* is located at a desired pressure acquisition site.

Each pressure membrane 230 comprises a material that is sufficiently flexible to be deformable in response to pressure or a change in pressure, and also having suitable radial, axial and tensile strengths to withstand the movements and forces necessary to insert, advance and place catheter 100 at a desired bodily location without rupturing, while exhibiting fast deformation return to nominal in order to sense pressures and changes in pressure without lag time. Suitable materials also advantageously have electrical conductivity in order to send signals to and relay sensed data and information from pressure membrane 230 via signal strip 240. Suitable materials additionally are biocompatible or can be covered or coated with a biocompatible material or composite of materials to enable their use within the body.

Example materials comprise carbon nanotubes and carbon nanotube sensors; silver nanoparticles; gold nanoparticles; other materials comprising nanotubes or nanoparticles; and/or other materials and/or composites thereof. In one embodiment, conformable carbon nanotube sensors (CNS) are used. CNSs are flexible and thin with large range and high sensitivity and use electrical conductivity between nanotubes over small gap distances. In another embodiment, silver nanoparticles are used. Silver nanoparticles are nanoparticles of silver or silver oxide. Still other embodiments can utilize other nanoparticle materials or other suitable materials. The CNS, silver nanoparticles, or other material can be embedded in a membrane carrier material, such as a silicon material or other base material, that has elastic properties suitable for the pressure membranes. The nominal resistance of the material is very low, but as the material deforms in shape its resistance changes, and this change in resistance provides an electrical signal that can be calibrated to indicate stretch, load, pressure, pressure differentiation, or other mechanical property changes. Other suitable materials also can be used, such as those exhibiting piezoelectric or piezoresistive effects or other suitable sensing technologies.

For example, when catheter 100 is in use and pressure sensor 210*a* is located within an artery, blood pressure within the artery and around catheter 100 can cause pressure membrane 230 to deform inwardly with respect lumen 206. Higher blood pressures can increase the inward deformation of pressure membrane, while lower blood pressures will cause a reduced inward deformation. These mechanical deformations of pressure membrane 230 can be sensed by each pressure sensor 210*a*-210*f* via a change in resistance or other characteristic, and signals from a pressure membrane 230 can be communicated via signal strip 240 to proximal portion 300 and from there to a user interface for calibration, calculation and/or presentation of sensed pressure-related data to a user. In embodiments, pressure sensors 210*a*-210*f* can sense pressures of varying levels, such as in a range of about 0 mmHg to about 160 mmHg in one embodiment. In other embodiments, other pressures may also be sensed by pressure sensors 210*a*-210*f*, including pressures within or higher than the aforementioned example range.

Referring also to FIGS. 1-3 and 5, signal strip 240 extends along distal portion 200 at least from proximal portion 300 to the most distal pressure sensor 210*f*. Signal strip 240 can comprise the same material as pressure membranes 230 (e.g., CNS, silver nanoparticles, etc.) or another electrically conductive material capable of communicating signals to and from pressure sensors 210*a*-210*f*, such as copper.

Distal portion 200 interfaces with proximal portion 300 at catheter cover 310 of proximal portion 300. Proximal portion 300 also comprises catheter hub 320 and electrical interface 330. Cover 310 is configured to engage with distal portion 200 to prevent blood, fluid and other materials from flowing upstream (i.e., from distal end 204 towards catheter hub 320). Cover 310 can be flexible and provides a substantially fluid-tight seal between distal portion 200 and catheter hub 320, in particular third leg 326 of catheter hub 320 (refer, e.g., to FIG. 6 and the related discussion infra). In some embodiments, cover 104 comprises a flexible plastic or other suitable material, such as an elastomer that will permit distal portion 200 of catheter 100 to slide, but prevent fluid from passing between distal portion 200 and catheter hub 320.

Figure 6:
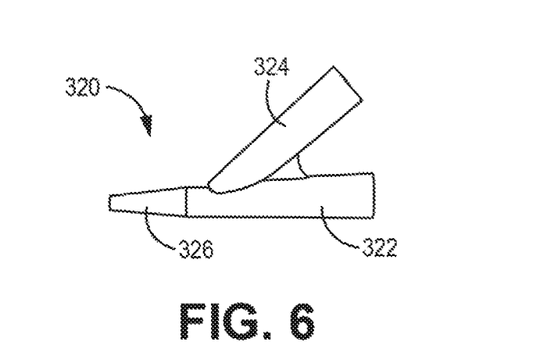
FIG. 6 is a side view of a proximal portion of a catheter hub according to an embodiment.

Referring also to FIG. 6, in the embodiment depicted catheter hub 320 has a substantially Y-shape. The Y-shape of catheter hub 320 is formed by three legs: first leg 322, second leg 324, and third leg 326. First leg 322 and third leg 326 are substantially collinear with one another, but in other embodiments the legs can be at a variety of relative angles with respect to one another. Third leg 326 interfaces with cover 310 and distal portion 200, and second leg 324 comprises electrical interface 330.

Figure 7:
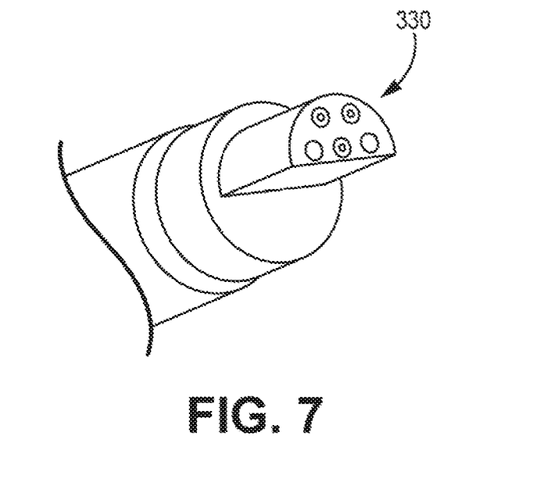
FIG. 7 is a perspective view of an electrical interface of a catheter according to an embodiment.

Referring also to FIG. 7, electrical interface 330 can comprise a three-pin micro-electrical interface connector in some embodiments. Thus, electrical interface 330 can comprise both mechanical and electrical interface components to physically and communicatively couple catheter 100 to an external device. The three pins comprise power, ground and signal (data) connections for communicating with pressure sensors 210*a*-210*f* via signal strip 240. Electrical interface 330 is depicted as a female connector, such that in embodiments a suitable male connector can be coupled to electrical interface 330 to, in turn, communicatively couple catheter 100 to a computing and/or display device for calibration, calculations, recording and displaying of data from pressure sensors 210*a*-210*f*. These female and male connectors can be reversed in other embodiments. Additionally, electrical interface 330 can comprise another type of connector, coupling or interface in other embodiments, including one that enables wireless communications between catheter 100 and an external device. The embodiment depicted in FIG. 7 is but one example.

In embodiments, the raw data signals, such as resistance or other sensed characteristics related to pressure membrane 230, from pressure sensors 210*a*-210*f* can be calibrated to pressure values, such as blood pressure values. The actual resistance or other values can be sensed, simultaneously at each pressure sensor 210*a*-210*f* location via the deformation or movement of each pressure sensor membrane 230, and reported, then calibrated to instantaneous pressure values. From these pressure values, pressure gradients (e.g., between different ones of pressure sensors 210a-210f, or gradients over time at individual ones of pressure sensors 210a-210f) can be calculated and reported. These calibrations and calculations can be carried out by a computer device (see, e.g., computer device 401 in FIG. 8), such as a computer, tablet, smartphone, server or other device, and related software. In embodiments, the computer device comprises a user interface and software, such as a patient monitoring device comprising a user interface for displaying patient information and data and internal computer components comprising software capable of receiving raw data sensed by pressure sensors 210a-210f, calibrating the raw data to calibrated pressure measurement data, calculating pressure gradients from the raw or calibrated data, and providing data for display by the patient monitor device. Examples of commercially available hardware and/or software for patient monitoring systems include those from SPACELABS, MATLAB and others, though other computer, tablet, smartphone, server or other devices can be used in embodiments. In some embodiments, an intermediary device, such as a computer, tablet, smartphone, server or other device can be coupled with electrical interface 330 to receive, calibrate, calculate, record and/or communicate pressure sensor data to a separate display device. In other embodiments, these functions can be integrated in a device or network. In general in various embodiments, catheter 100 can easily integrate with existing clinical display and recording devices to carry out the functions discussed herein, thereby avoiding the need for investment in additional capital equipment or dedicated systems beyond catheter 100 itself. This can be done by a cable with a standard connector capable of communicatively coupling catheter 100, via electrical interface 330, with a clinical display and recording or other device.

Figure 8:
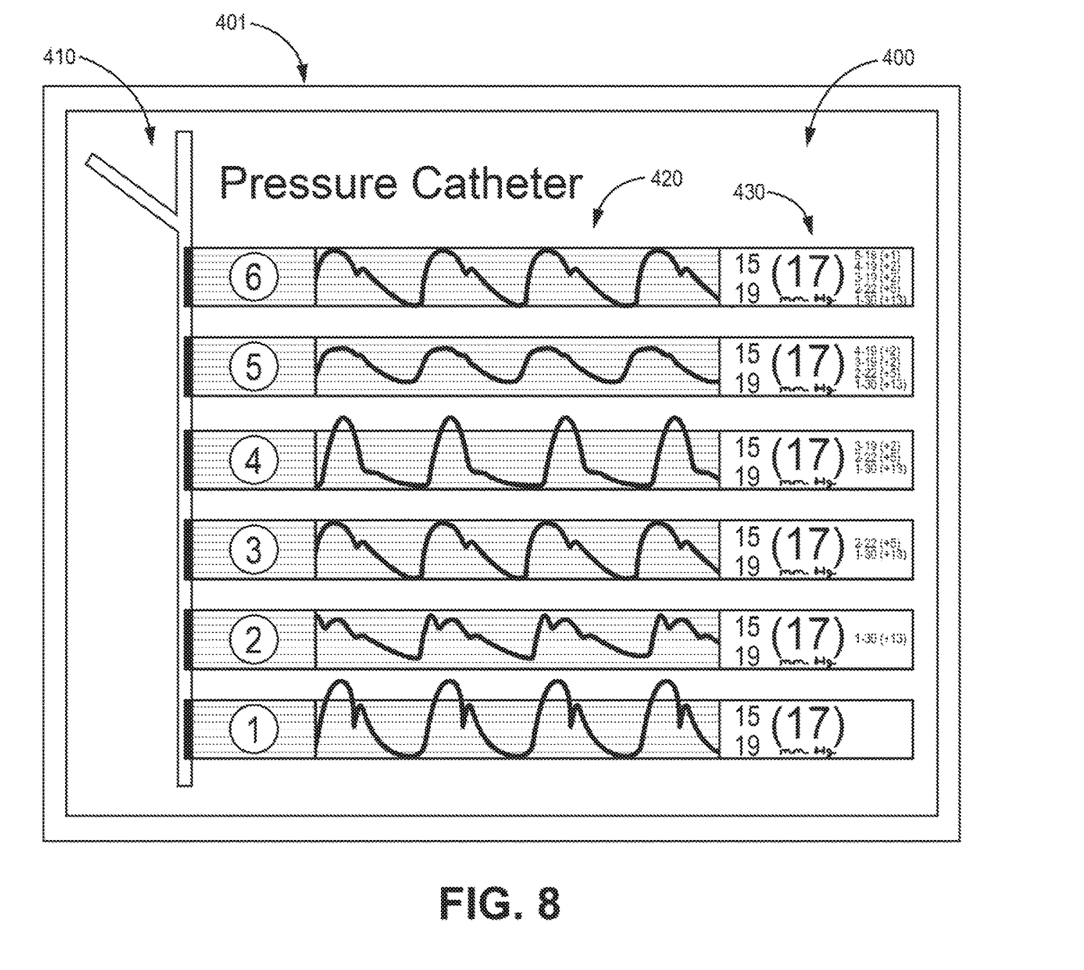
FIG. 8 is a screenshot of a user interface presented by a computer device according to an embodiment.

An example user interface 400 presented by a computer device 401 is shown in FIG. 8. User interface 400 includes a visual representation of catheter 100 and pressure sensors 210a-210f at 410. The data from each pressure sensor 210a-210f also can be labeled (e.g., 1, 2, 3, etc.; A, B, C, etc.) in some way to make identification of data and its source location easy for a physician or other clinician. Real-time graphical pressure data for each pressure sensor 210a-210f can be displayed in a central portion 420, while an actual current measurement, high/low measurements at that location, and/or calculated gradient data can be displayed at portion 430. Gradients can be calculated and selected for display in a variety of ways. In FIG. 8, sensor location 1 (e.g., pressure sensor 210f) shows no gradient information. Sensor location 2 (e.g., pressure sensor 210e) includes calculated pressure gradient data with respect to sensor location 1. Sensor location 3 (e.g., pressure sensor 210d) includes calculated pressure gradient data with respect to sensor locations 1 and 2. This continues to sensor location 6 (e.g., pressure sensor 210a), which includes calculated pressure gradient data with respect to all of sensor locations 1-5. Still other gradients could be calculated and displayed, or some gradients shown in FIG. 8 omitted from display in other embodiments.

Figure 9:
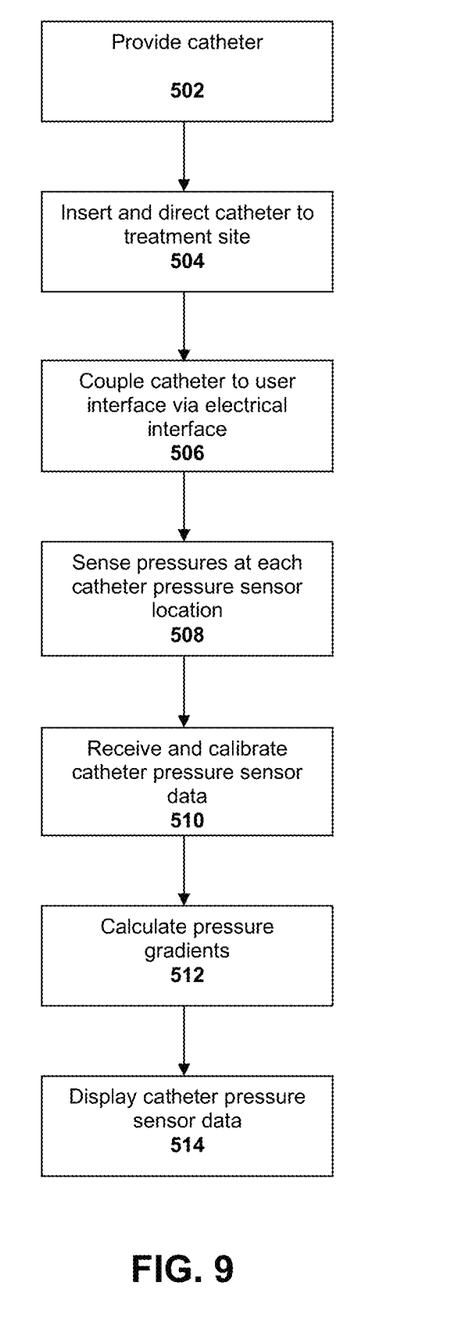
FIG. 9 is a flowchart of a method according to an embodiment.

In use, and referring to FIG. 9, a multi-focal intravascular pressure catheter is provided at 502. At 504, the catheter is inserted and directed to a desired treatment site. At 506, the catheter is coupled, via its electrical interface, to a user interface device. Pressures at each pressure sensor location along the catheter can be sensed simultaneously at 508, and data can be communicated from the catheter via the electrical interface to a device that can calibrate raw data from the catheter pressure sensors at 510. In some embodiments, the calibration can be pre-performed or is unnecessary and can be omitted. At 512, pressure gradients can be calculated between pressure sensor locations along the catheter. A single gradient can be calculated, or multiple gradients can be calculated. At 514, pressure sensor data, such as raw data, calibrated pressure sensor data, gradient data, and/or other data, can be displayed on a user interface and updated periodically or in real time. Data can also, optionally, be logged or reported, such as in an electronic medical record, data file, or other location.

In embodiments, one or more of the activities of FIG. 9 can be omitted (e.g., calibration of pressure sensor data, or calculation of gradients) or reordered (e.g., the catheter can be coupled to the user interface at 506 before 504, some data can be displayed before gradients are calculated). Still other activities or tasks can be added. For example, pressure data can be requested on-demand between 508 and 510 via the catheter or user interface, and/or the location of the catheter and/or the position of any particular pressure can be visually verified via a radiopaque band using a fluoroscope.

In one embodiment, a multi-focal intravascular pressure catheter system can comprise catheter 100, including distal portion 200 and proximal portion 300, wherein distal portion 200 comprises a plurality of pressure sensors, each pressure sensor comprising a pressure sensor membrane that is deformable in response to intravascular blood pressure or some other quantity, and the plurality of pressure sensors are coupled via a signal strip to proximal portion 300 for communication to a user interface for calibration of pressure sensor data and calculation of pressure gradients along distal portion 200. The pressure sensor membrane can comprise a nanoparticle, nanotube or other material in embodiments.

In another embodiment, a multi-focal intravascular pressure catheter system can comprise catheter 100, including distal portion 200 and proximal portion 300, wherein distal portion 200 comprises a plurality of pressure sensors, each pressure sensor comprising a pressure sensor membrane that is deformable in response to intravascular blood pressure or some other quantity, and the plurality of pressure sensors are coupled via a signal strip to proximal portion 300 for communication to a user interface for calibration of pressure sensor data and calculation of pressure gradients along distal portion 200, a connector and cable suitable for coupling electrical interface 330 of proximal portion 300 with a computer device comprising software and hardware, wherein the software is configured to calibrate raw pressure sensor data and calculate at least one pressure gradient between individual ones of the plurality of pressure sensors, and wherein the hardware is configured to display a user interface to present at least one of the calibrated data or the calculated pressure gradients. In yet another embodiment, the multi-focal intravascular pressure catheter system can comprise the computer device, hardware and/or software.

Embodiments thus are related to multi-focal intravascular pressure sensing catheters. Various embodiments discussed herein can provide numerous advantages with respect to conventional devices, including applicability to a variety of catheter and vessel sizes, availability of multi-focal pressure information in real-time, availability of pressure gradient information without conducting a pullback study, reduced cost via pressure sensor materials and configurations in embodiments, and a more stable working platform. These embodiments can address a need in the medical industry and can also have applicability to other, non-medical applications, including measuring pressures in aquifers, well systems, pipeline systems and other applications. In these applications, the size and configuration of the catheter system can change and be scaled up as needed. For instance, example dimensions suitable for medical applications and provided herein in mm or cm can instead be measured in meters or more. In other words, the particular example applications and dimensions given herein are only examples, and those skilled in the art will recognize that scaling up (or even down) may be considered for applications in other fields.

Additionally, the computer, computing device, tablet, smartphone, server, and hardware mentioned herein can be any programmable device(s) that accepts analog and/or digital data as input, is configured to process the input according to instructions or algorithms, and provides results as outputs. In an embodiment, the processing systems can include one or more central processing units (CPUs) configured to carry out the instructions stored in an associated memory of a single-threaded or multi-threaded computer program or code using conventional arithmetical, logical, and input/output operations. The associated memory can comprise volatile or non-volatile memory to not only provide space to execute the instructions or algorithms, but to provide the space to store the instructions themselves. In embodiments, volatile memory can include random access memory (RAM), dynamic random access memory (DRAM), or static random access memory (SRAM), for example. In embodiments, non-volatile memory can include read-only memory, flash memory, ferroelectric RAM, hard disk, floppy disk, magnetic tape, or optical disc storage, for example. The foregoing lists in no way limit the type of memory that can be used, as these embodiments are given only by way of example and are not intended to limit the scope of the claims.

In other embodiments, the processing system or the computer, computing device, tablet, smartphone, server, and hardware, can include various engines, each of which is constructed, programmed, configured, or otherwise adapted, to autonomously carry out a function or set of functions. The term engine as used herein is defined as a real-world device, component, or arrangement of components implemented using hardware, such as by an application specific integrated circuit (ASIC) or field-programmable gate array (FPGA), for example, or as a combination of hardware and software, such as by a microprocessor system and a set of program instructions that adapt the engine to implement the particular functionality, which (while being executed) transform the microprocessor system into a special-purpose device. An engine can also be implemented as a combination of the two, with certain functions facilitated by hardware alone, and other functions facilitated by a combination of hardware and software. In certain implementations, at least a portion, and in some cases, all, of an engine can be executed on the processor(s) of one or more computing platforms that are made up of hardware that execute an operating system, system programs, and/or application programs, while also implementing the engine using multitasking, multithreading, distributed processing where appropriate, or other such techniques.

Accordingly, it will be understood that each processing system can be realized in a variety of physically realizable configurations, and should generally not be limited to any particular implementation exemplified herein, unless such limitations are expressly called out. In addition, a processing system can itself be composed of more than one engine, sub-engines, or sub-processing systems, each of which can be regarded as a processing system in its own right. Moreover, in embodiments discussed herein, each of the various processing systems may correspond to a defined autonomous functionality; however, it should be understood that in other contemplated embodiments, each functionality can be distributed to more than one processing system. Likewise, in other contemplated embodiments, multiple defined functionalities may be implemented by a single processing system that performs those multiple functions, possibly alongside other functions, or distributed differently among a set of processing system than specifically illustrated in the examples herein.

Various embodiments of devices, systems and methods have been described herein. These embodiments are given only by way of example and are not intended to limit the scope of the invention. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the invention.

Persons of ordinary skill in the relevant arts will recognize that the invention may comprise fewer features than illustrated in any individual embodiment described above. The embodiments described herein are not meant to be an exhaustive presentation of the ways in which the various features of the invention may be combined. Accordingly, the embodiments are not mutually exclusive combinations of features; rather, the invention can comprise a combination of different individual features selected from different individual embodiments, as understood by persons of ordinary skill in the art. Moreover, elements described with respect to one embodiment can be implemented in other embodiments even when not described in such embodiments unless otherwise noted. Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended. Furthermore, it is intended also to include features of a claim in any other independent claim even if this claim is not directly made dependent to the independent claim.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims for the present invention, it is expressly intended that the provisions of Section 112, sixth paragraph of 35 U.S.C. are not to be invoked unless the specific terms "means for" or "step for" are recited in a claim.

The invention claimed is:

1. A multi-focal intravascular pressure catheter comprising:
   a proximal portion comprising an electrical interface;
   a distal portion comprising at least one lumen, the distal portion configured to interface with the proximal portion;

a plurality of pressure sensors spaced apart along the distal portion, each of the plurality of pressure sensors each comprising at least one pressure membrane made of a suitable material that exhibits change a resistance in response to mechanical deformation, the at least one pressure membrane arranged over a plurality of apertures in the distal portion and configured to deform in response to a pressure or a lack of pressure acting on the at least one pressure membrane, the plurality of pressure sensors spaced apart along the distal portion such that differential pressure gradients can be determined among the plurality of pressure sensors; and a signal strip extending from the proximal portion and along the distal portion, the signal strip electrically coupled with the electrical interface and the at least one pressure membrane of each of the plurality of pressure sensors to provide an electrical signal related to a deformation or lack of a deformation of the at least one pressure membrane to the electrical interface and such that multiple differential pressure gradients among the plurality of pressure sensors are simultaneously presented.

2. The catheter of claim 1, wherein the pressure membrane comprises at least one of carbon nanotubes, carbon nanotubes sensors, silver nanoparticles, gold nanoparticles, a material comprising nanoparticles, or a material comprising nanotubes.

3. The catheter of claim 2, wherein the at least one pressure membrane comprises conformable carbon nanotubes sensors (CNS).

4. The catheter of claim 1, wherein the signal strip comprises at least one of carbon nanotubes, carbon nanotubes sensors, silver nanoparticles, gold nanoparticles, a material comprising nanoparticles, a material comprising nanotubes, or copper.

5. The catheter of claim 1, wherein a size of the catheter is in a range selected from the group consisting of: at least 3 French; and at least 5 French.

6. The catheter of claim 1, wherein a length of the catheter is in a range selected from the group consisting of: at least 40 centimeters (cm); at least 60 cm; and at least 90 cm.

7. The catheter of claim 1, wherein the distal portion comprises two concentric lumens, a first inner lumen and a second outer lumen, wherein the plurality of apertures is arranged in the outer lumen.

8. The catheter of claim 1, wherein at least one of the plurality of pressure sensors comprises two apertures arranged opposite one another on a circumference of the distal portion, a first pressure membrane arranged over one aperture and a second pressure membrane arranged over the other aperture.

9. The catheter of claim 8, wherein adjacent ones of the plurality of pressure sensors are rotated 90 degrees with respect to one another.

10. The catheter of claim 1, wherein a diameter of the plurality of apertures is about 0.01 inches to about 0.025 inches.

11. The catheter of claim 1, wherein the plurality of pressure sensors is configured to sense a pressure in a range of about 0 mmHg to about 160 mmHg.

12. The catheter of claim 1, wherein the electrical interface comprises a multi-pin micro-electrical connector.

13. The catheter of claim 12, wherein the electrical interface is configured to electrically couple the catheter with a computer device configured to present data related to the electrical signal related to a deformation or lack of a deformation of the at least one pressure membrane of the plurality of pressure sensors.

14. The catheter of claim 13, wherein the electrical interface is configured to provide raw data signals from the plurality of pressure sensors to the computer device, and wherein the computer device is configured to calibrate the raw data signals to pressure values.

15. The catheter of claim 14, wherein the computer device is configured to calculate the at least one pressure gradient between different ones of the plurality of pressure sensors.

16. The catheter of claim 15, wherein the computer device is configured to cause to be displayed at least one of the raw data signals, the pressure values or the at least one pressure gradient.

17. The catheter of claim 1, wherein the proximal portion comprises a cover, and wherein the distal portion interfaces with the proximal portion at the cover.

18. A catheter system comprising: a multi-focal intravascular pressure catheter comprising:

a proximal portion comprising an electrical interface, a distal portion comprising at least one lumen, the distal portion configured to interface with the proximal portion, a plurality of pressure sensors spaced apart along the distal portion, each of the plurality of pressure sensors each comprising at least one pressure membrane made of a suitable material that exhibits change a resistance in response to mechanical deformation, the at least one pressure membrane arranged over a plurality of apertures in the distal portion and configured to deform in response to a pressure or a lack of pressure acting on the at least one pressure membrane, the plurality of pressure sensors spaced apart along the distal portion such that differential pressure gradients can be determined among the plurality of pressure sensors; and a signal strip extending from the proximal portion and along the distal portion, the signal strip electrically coupled with the electrical interface and the at least one pressure membrane of each of the plurality of pressure sensors to provide an electrical signal related to a deformation or lack of a deformation of the at least one pressure membrane to the electrical interface and such that multiple differential pressure gradients among the plurality of pressure sensors are simultaneously presented; and a cable electrically coupleable to the electrical interface to provide the electrical signal related to a deformation or lack of a deformation of the at least one pressure membrane from the electrical interface to a computer device.

* * * * *